United States Patent [19]

Smutny

[11] 4,436,946

[45] Mar. 13, 1984

[54] PREPARATION OF PROPYLENE AND BUTYLENE DIMERS USING PALLADIUM CYANIDE AS CATALYST

[75] Inventor: Edgar J. Smutny, Houston, Tex.

[73] Assignee: Shell Oil Company, Houston, Tex.

[21] Appl. No.: 442,999

[22] Filed: Nov. 19, 1982

[51] Int. Cl.³ .................... C07C 3/10; C07C 3/12; C07C 3/18
[52] U.S. Cl. .................... 585/510; 585/527; 585/531; 502/175
[58] Field of Search .............. 585/510, 527, 530, 531; 252/438, 443, 472

[56] References Cited

U.S. PATENT DOCUMENTS 3,758,626  9/1973  Arganbright et al. .............. 585/510
3,853,786  12/1974  Forni et al. ........................ 585/510

*Primary Examiner*—Delbert E. Gantz
*Assistant Examiner*—A. Pal

[57] ABSTRACT

This invention is a process for the selective conversion of propylene and the n-butylenes to their dimers, in the presence of a heterogeneous palladium cyanide catalyst. The product dimers are predominantly of straight-chain structure.

11 Claims, No Drawings

PREPARATION OF PROPYLENE AND BUTYLENE DIMERS USING PALLADIUM CYANIDE AS CATALYST

BACKGROUND OF THE INVENTION

The present invention relates to a process for the dimerization of propylene and the n-butylenes by reaction in the presence of a heterogeneous palladium cyanide catalyst.

The mono-olefinic dimers of propylene and the n-butylenes have recognized utility as intermediates in the synthesis of lubricants, plasticizes and surface active agents, particularly alcohols and alkylates. In the past, commercial production of mono-olefins in the $C_6$ to $C_8$ range has largely been achieved through the catalytic oligomerization of ethylene. Economic incentive has developed, however, for the use of other feedstocks, particularly propylene and the butylenes.

Under common conventional practice, propylene and butylene have been converted to dimers by reaction in the presence of a strong acid, particularly sulfuric acid, phosphoric acid, or boron trifluoride. The products of such conversions have substantial branching in the dimer molecules. An object of the present invention is a process which is selective in the production of dimers having limited branching in the molecular structure.

With regard to general aspects of the present invention relating to propylene and butylene dimerization reactions catalyzed by palladium salts, it is known in the art (U.S. Pat. No. 3,758,626 to R. P. Arganbright) that dimerization of olefins can be accomplished in the presence of palladium halide, sulfate or nitrate salts supported on materials such as alumina or silica alumina. Palladium chloride and palladium nitrate are said to be particularly preferred, and no mention is made in the patent of the use of palladium cyanide. Experimental examples indicate very low levels for conversion of propylene to its dimers.

A. D. Ketley et al (Inorganic Chemistry, Vol. 6, No. 4, April 1967, pp. 657–663) also disclose the dimerization of propylene by palladium chloride. The catalysis is homogeneous with the palladium chloride present as a complex with propylene in solution together with a solvent such as $CCl_4$, $C_2H_5Cl$, t-$C_4H_9Cl$, $CHCl_3$, $CH_2Cl_2$, or anisole. The products of this dimerization are strongly dependent upon the nature of the solvent.

With regard to more particular aspects of the invention relating to a palladium cyanide catalyst, it is further known from the above-referenced publication of Ketley et al and from U.S. Pat. No. 3,535,302 to Ketley that ethylene can be dimerized in the presence of palladium cyanide. However, when propylene was utilized as a reactant instead of ethylene, the publication and the patent indicate that a reaction either with or without a solvent yields only a polymeric product. No reaction was observed for butylenes.

Y. Odaira et al (J.A.C.S., Vol. 88, No. 17, Sept. 5, 1966, p. 4106) disclose that the reaction of propylene in the presence of palladium cyanide and a polar solvent yields the cyanation products HCN, methacrylonitrile, 3-butenenitrile, crotononitrile, isobutyronitrile, and butyronitrile. In nonpolar solvents, $Pd(CN)_2$ was said to lead almost exclusively to the conversion of propylene to high polymers.

A. Sen et al (J.A.C.S., 1981, Vol. 103, p. 4627; Organometallics, 1982, Vol. 1, p. 415; and a paper presented to the August 1981 International Symposium on Transition Metal Catalyzed Polymerization: Unsolved Problems) have recently reported that certain metal complexes, including $Pd(CH_3CN)_4(BF_4)_2$, are active as homogeneous catalysts for the dimerization, oligomerization, and polymerization of olefins, apparently to relatively highly branched product molecules.

SUMMARY OF THE INVENTION

It has now been found that propylene and the n-butylenes can be converted with good selectivity to their dimers in a process utilizing a heterogeneous palladium cyanide catalyst. The product dimers are characterized by limited branching in the molecule.

The invention may be briefly described as a process for the dimerization of propylene and/or n-butylenes which comprises steps for (a) contacting under mechanical agitation an olefin reactant selected from the group consisting of propylene, 1-butene, 2-butene, and mixtures thereof with a heterogeneous palladium cyanide catalyst at a temperature in the range from about 50° C. to 150° C., the quantity of said palladium cyanide being between about 0.01 and 10 percent by weight calculated on weight of olefin reactant, and (b) recovering olefin dimers from the reaction product solution resulting from step (a).

Mechanical agitation of the reaction mixture and limitation upon the quantity of palladium cyanide utilized as catalyst have both been found necessary to accomplish conversion to dimers rather than to a polymeric product. Addition of a complexing agent or other solvent is unnecessary. The product dimers are in large part of straight-chain structure. With a propylene reactant, for instance, greater than 70% of the product dimers are typically normal hexenes.

DESCRIPTION OF THE PREFERRED EMBODIMENTS

The process of the invention is intended for application to the preparation of dimers from an olefin reactant selected from the group consisting of propylene, 1-butene, 2-butene, and mixtures thereof. The term dimers is used herein to describe the $C_6$ addition product of two propylene molecules, the $C_8$ addition product of two butylene molecules, or the $C_7$ addition product of propylene and butylene. Propylene is prefered as reactant in the invention.

A further necessary element of the invention is the use of a heterogeneous palladium cyanide catalyst. Other transition metal cyanide salts, e.g., platinum cyanide and nickel cyanide, are not effective catalysts under conditions of the invention. Palladium cyanide is a well known and commercially available material.

The form in which the palladium cyanide is used is generally not critical to the invention. Preference may be expressed, however, for a catalyst which has been ground into a fine particulate to expose a relatively high surface area. The palladium cyanide may be applied alone or may be supported on or otherwise combined with inert solid carriers. Particularly prefered are catalysts prepared by grinding or ball milling the palladium cyanide together with one or more essentially inert solids such as carbon, silica, and the cyanides of platinum, nickel, zinc, and copper. As a rule, such grinding of the catalyst, either alone or together with such supporting materials, increases its activity and/or selectivity to dimers in the process, although excessive grinding may have the opposite result.

Activity may also be enhanced if the catalyst is thoroughly washed with water or an aqueous acid solution (e.g., for several hours) before it is contacted with the olefin reactant.

For carrying out the process of the invention, the olefin reactant and the palladium cyanide are charged to a suitable pressure reactor equipped for mechanical agitation of the solid catalyst and the liquid reactant. The presence of a substance capable of converting the palladium cyanide into a form which is soluble in the reaction mixture is unnecessary and inconsistent with the intended application of a heterogeneous catalyst. Accordingly, the process is carried out essentially in the absence of any such substance. Non-polar reaction solvents (other than substances capable of solubilizing the palladium cyanide) may be added to the reaction mixture if desired. The presence of certain organic solvents, such as toluene, mesitylene, nitrobenzene and benzonitrile has been found to enhance process conversion and/or selectivity. However, the use of a significant quantity of such a reaction solvent often proves to be of disadvantage when consideration is given to its recovery from the product mixture, and the process of the invention is preferably carried out in the absence of any substantial quantity of such solvents. Most preferably, the reaction mixture is essentially free of any materials which could be considered reaction solvents, with the exception of olefin reactants and reaction products.

It has been found that process conversion and/or selectivity can alternatively be improved by the presence in the catalyst and reactant mixture of a relatively small quantity of one or more of certain polar reaction accelerators. Water and certain acids, including for example, halogen acids, sulfuric acid, phosphoric acid, acetic acid, formic acid, trifluoroacetic acid and trifluorosulfuric acid, are very suitable for use as accelerators. Hydrofluoic acid is particularly prefered. The quantity of such accelerator is not critical, and as little as one percent by weight calculated on palladium cyanide may be effective. Preferably, when an acid is applied as the accelerator it is used in a quantity between about 5 and 100%w, based on palladium cyanide. A larger quantity, for example, up to about ten times by weight that of the $Pd(CN)_2$, may be utilized, however, and is preferred when the added accelerator is water.

The particular equipment employed for mechanical agitation of the reactant and catalyst are not critical to the invention—suitable mixing means include driven impellers, fluid jets, flow baffles, etc. Continual forced circulation of reactant liquid over the catalyst surface is found to enhance process selectivity to the desired dimers. Agitation also inhibits deposition of polymeric by-products on the solid palladium cyanide particles and a resulting loss of catalyst activity.

The invention is necessarily carried out using a limited quantity of palladium cyanide relative to the olefin reactant with which it is contacted. Excessive quantities of catalyst promote formation of products other than dimers, particularly the production of polymers as suggested in the prior art. A quantity of palladium cyanide that is at least about 0.01 percent by weight (%w) calculated on olefin reactant is typically effective for purposes of the invention. Preferably, the quantity of palladium cyanide is limited to about 10%w calculated on olefin reactant. Between about 0.1 and 6%w catalyst, calculated on this same basis is considered more preferred, and between about 0.5 and 4%w most preferred. Particularly good results have been obtained using a quantity of catalyst that is between about 1 and 3%w, calculated on olefin reactant.

Temperature of the catalyst and olefin reactant mixture during the course of the invention is suitably between about 50° C. and 150° C., preferably between about 70° C. and 130° C., more preferably between about 80° C. and 120° C., and most preferably about 100° C. Prolonged exposure of of the palladium cyanide catalyst to temperatures in excess of 150° C. has been observed to result in a loss of catalyst activity. Process pressure is not critical. The reaction is very suitably carried out at the pressure of the liquid olefin reactant and product (or reactant, product and solvent) mixture at the operating temperature. Pressure can suitably be increased above this equilibrium level, for instance, by introduction of an inert gas, although this has not been found to benefit either conversion or selectivity. Similarly, reaction time is not critical to the invention. However, preference can be stated for a contact with catalyst that is between about 1 and 50 hours for a propylene reactant and between about 4 and 100 hours for a butylene reactant.

In distinction to conventional dimerization processes, the process of the invention is selective to the production of dimer having limited branching in the molecule. The dimer products are comprised in very substantial proportion of straight chain (linear) alkenes and of alkenes having a single methyl substituent at an internal carbon atom. In the case of propylene dimers, about 50 to 95 percent are linear hexenes, with the remainder almost entirely 2-methylpentenes. For butylene dimers, about 30 to 40 percent are linear. Limited branching in the product molecule is particularly important when the dimers are utilized as intermediates in the synthesis of detergent chemicals, for which it is recognized that highly branched carbon chains are undesirable from the standpoint of biodegradation.

Following contact between the olefin reactant and the palladium cyanide catalyst, dimer is separated from the reaction mixture, which also contains lesser amounts of trimer, higher oligomers and other by-products in solution and solid catalyst and precipitated polymer. Under a preferred method for dimer recovery, unreacted propylene and/or butylene are removed by evaporation and solid catalyst and polymer are removed by filtration, leaving a solution from which dimer is then separated by fractionation.

The invention is further illustrated in the following examples. Selectivities reported are calculated on the basis of the total quantity of dimer, trimer, oligomer, and polymer recovered from the product and isolated. No significant amount of any other process product was observed.

EXAMPLE 1

To a stirred 80 ml autoclave reactor at dry ice temperature were added 713 millimoles (mm) of propylene and 3.1 mm of commercial palladium cyanide powder (Engelhardt). The mixture was heated to 100° C. and maintained at that temperature for two hours. A maximum pressure of about 825 psig was recorded. Six percent of the propylene was converted to product of the following distribution: 60%w dimers, 7%w trimers, 8%w higher oligomers (present in solution in the liquid reaction mixture), and about 25%w polymer (i.e., as precipitate from the liquid reaction mixture).

EXAMPLE 2

Commercial palladium cyanide was ground and sieved to particles having a diameter between about 15 and 42 microns. The reactor was charged with 3.1 mm of these particles and the procedures of Example 1 again followed. After a two hour reaction at 100° C., 9% of the propylene reactant was converted to a product distribution: 64%w dimers, 12%w trimers, 7%w higher oligomers, and 17%w polymer. After a 16 hour reaction, conversion was 19% to a product mixture 59%w dimers, 15%w trimers, 8%w higher oligomers, and 18%w polymers.

Palladium cyanide particles having a diameter greater than about 88 microns were also obtained by grinding and tested as propylene dimerization catalyst with comparable results.

EXAMPLE 3

The general procedures of Example 1 were again followed, using 6.3 mm commercial palladium cyanide as catalyst and 708 mm propylene reactant. A two hour reaction at 100° C. (775 psig maximum pressure) converted 19% of the propylene to a mixture of 66%w dimers, 11%w trimers, 8%w higher oligomers and about 15%w polymers. In a sixteen hour reaction under comparable conditions, converstion reached 31% and the product distribution was 56%w dimers, 11%w trimers, 9%w higher oligomers, and about 24%w polymers.

EXAMPLE 4

The procedures of Example 1 were again followed using as catalyst a ground commercial palladium cyanide. Thirty ml of mesitylene reaction solvent was also added to the autoclave. A two hour reaction at 100° C. (maximum pressure 757 psig) resulted in a conversion of 10% and a product distribution of 69%w dimers. 14%w trimers, 8%w higher oligomers, and about 9%w polymers.

When only 368 mm of propylene was charged together with the 3.1 mm of ground catalyst and the 30 ml solvent, the two hour reaction resulted in an increase in conversion to 22%, but in a decrease in product dimers selectivity to about 53%w.

EXAMPLE 5

A representative sample of the dimer product prepared in accordance with the procedures of Examples 1–4 was analyzed by NMR. About 73% of the product dimer molecules were found to have a straight chain structure, while the remaining 27% consisted essentially of 2-methylpentenes. The results of an NMR analysis of the dimers are presented in Table I.

TABLE I

| Dimer Structure | Percent of Total Dimers |
| --- | --- |
| Straight chain Dimer | |
| 1-hexene | 4% |
| 2-hexene cis | 15% |
| trans | 28% |
| 3-hexene cis | 7% |
| trans | 19% |
| TOTAL | 73% |
| Branched chain dimer | |
| 2-methyl-1-pentene | 8% |
| 2-methyl-2-pentene | 13% |
| 2-methyl-3-pentene | 5% |
| 2-methyl-4-pentene | 1% |
| TOTAL | 27% |

EXAMPLE 6

A dimerization of propylene in accordance with the invention was carried out in a 300 ml autoclave. Commercial palladium cyanide (3.15 mm) and propylene (90 g) were added to the autoclave at dry ice temperature. The mixture was heated to 100° C. and maintained at that temperature for 20 hours, with continual stirring. Conversion of 8% of the propylene yielded as product 67%w dimer, 12%w trimer, 7%w higher oligomers, and about 14%w polymers.

EXAMPLE 7

The procedures of Example 6 were followed, with the further addition of toluene (10 g) to the autoclave. Reaction for 20 hours at 100° C. resulted in a 10% propylene conversion to the product: 69%w dimer, 10%w trimer, 6%w oligomers, and 15%w polymers.

EXAMPLE 8

To the 80 ml autoclave reactor at dry ice temperature were added 3.1 mm of commercial palladium cyanide and 667 mm of 1-butene reactant. The mixture was heated to 100° C. and maintained at that temperature with stirring for 40 hours: A maximum pressure of about 275 psig was recorded. Conversion of the 1-butene was 3% to a product mixture containing about 40 to 50%w dimer. After hydrogenation, the dimer product was analyzed as about 35–40% linear octane and 60–65% 3-methylheptane.

EXAMPLE 9

The procedures of Example 8 were generally followed, with the addition to the autoclave of 3.1 mm palladium cyanide (ground to fine particulate) and 615 mm 1-butene. Reaction for 16 hours at 100° C. resulted in a conversion of about 3%; roughly one-half of the product by weight consisted of C₈ dimers.

EXAMPLE 10

Again following the general procedures of Example 8, the autoclave was charged with 549 mm 1-butene, 3.1 mm ground palladium cyanide, and as accelerator three drops of an aqueous 48%w hydrofluoric acid solution. Conversion after 16 hours was 7% to a product containing about 50%w dimers.

EXAMPLE 11

The general procedures of Example 10 were followed, using 6.3 mm ground palladium cyanide, six drops of the hydrofluoric acid solution, and 544 mm 1-butene. Conversion was 16% after 16 hours, with a slightly improved selectivity to dimers.

EXAMPLE 12

Dimerization reactions of cis and trans 2-butenes were carried out generally according to the methods of Examples 8–11. Resulting dimer selectivities were again about 50%w. Rates of conversion for cis 2-butene was comparable to those for 1-butene. Rates for trans 2-butene were substantially slower.

EXAMPLE 13

The procedures of Example 1 were repeated. In this case, however, before introduction into the autoclave the catalyst was stirred in water for 20 hours and the dried under vacuum for 65 hours. As a result of this catalyst treatment, conversion and selectivity were both increased.

EXAMPLES 14–16

A series of experiments were carried out to illustrate the influence of the presence of a small quantity of an acidic accelerating agent upon conversion of propylene and selectivity to dimer. The procedures of Example 1 were followed, with the further addition to the autoclave of one drop of 50% acetic acid, 19% hydrochloric acid, or 28% phosphoric acid. Conversions were about 7%, 11%, and 15% respectively, and selectivities to dimers about 66%, 68%, and 69%, by weight.

COMPARATIVE EXAMPLES

Dimerizations of propylene were attempted using nickel and platinum cyanide as catalysts, and thus not in accordance with the invention. To the 80 ml autoclave reactor were charged 30 g of propylene and 0.5 g of the nickel cyanide or platinum cyanide. No conversion of the propylene was found after sixteen hours at a temperature of 100° C.

EXAMPLE 17

Palladium cyanide was ball milled with an equal quantity (by mole) of platinum cyanide by grinding in a Fritscht Pulverisette machine. The resulting mixture was then tested as a catalyst in the process of the invention. A total of about 1.2 g of the resulting mixture, containing 3.1 mm palladium cyanide, was introduced into the 80 ml reactor together with 713 mm propylene. A two hour reaction at 100° C. resulted in a 12% conversion of propylene and a product mixture of which about 70%w was dimer. Reaction under like conditions for sixteen hours achieved a 41% conversion and a selectivity to dimer of about 55 to 60%w. Polymer production in each case was only about 6 to 8%w. Increasing the molar ratio of palladium cyanide to platinum cyanide to 1.6 to 1 and charging the reactor with 1.0 g of the mixture (containing 3.1 mm palladium cyanide) increased conversion to 43%.

EXAMPLE 18

Ball milled mixtures of palladium cyanide with nickel cyanide, with cobalt cyanide and with zinc cyanide were prepared and tested generally according to the procedures of Example 17. Conversions of 22%, 17%, and 19% were observed after 16 hours reactions, with selectivities to dimers of between 55 and 60%w.

EXAMPLE 19

For each of the above-described examples, propylene (or butylene) reactant was vented (flash evaporated) from the product mixture, leaving a liquid solution of dimers, trimers and higher oligomers and a solid polymer and catalyst phase. After its physical separation from the solid phase, e.g., by filtering, the liquid solution was distilled at atmospheric pressure and the dimers recovered overhead. In the case of propylene dimer preparation, the distilled fraction was obtained at a boiling point in the range from about 68° to 75° C.

I claim as my invention:

1. A process for the selective dimerization of propylene and/or n-butylenes which comprises steps for (a) contacting under mechanical agitation an olefin reactant selected from the group consisting of propylene, 1-butene, 2-butene, and mixtures thereof with a heterogeneous palladium cyanide catalyst at a temperature in the range from about 50° C. to 150° C., the quantity of said palladium cyanide being between about 0.01 and 10 percent by weight calculated on the weight of olefin reactant, to produce a reaction product solution containing olefin reactant dimers, and (b) recovering said dimers from said product solution.

2. The process of claim 1, wherein the contact between olefin reactant and palladium cyanide catalyst is carried out in a reaction mixture essentially free of added reaction solvent.

3. The process of claim 2, wherein the olefin reactant is propylene.

4. The process of claim 3, wherein the quantity of palladium cyanide is between about 0.1 and 6 percent by weight, calculated on the weight of olefin reactant.

5. The process of claim 4, wherein the quantity of palladium cyanide is between about 0.5 and 4 percent by weight, calculated on the weight of olefin reactant.

6. The process of claim 1, claim 2, claim 3, claim 4, or claim 5, wherein the contact between olefin reactant and palladium cyanide catalyst is carried out in the presence of water or an acid as a reaction accelerator.

7. The process of claim 6, wherein the accelerator is hydrofluoric acid in a quantity between about 5 and 100%w calculated on palladium cyanide.

8. The process of claim 1, claim 2, claim 3, claim 4, or claim 5, wherein the catalyst comprises palladium cyanide on an essentially inert solid support.

9. The process of claim 8, wherein the support is platinum cyanide.

10. The process of claim 8, wherein the catalyst is prepared by ball milling the palladium cyanide with the inert support.

11. The process of claim 9, wherein the catalyst is prepared by ball milling the palladium cyanide with the inert support.

* * * * *